United States Patent [19]
Bloebaum

[11] Patent Number: 4,964,868
[45] Date of Patent: * Oct. 23, 1990

[54] KNEE PROSTHESIS

[75] Inventor: Roy D. Bloebaum, Phoenix, Ariz.

[73] Assignee: Harrington Arthritis Research Center, Phoenix, Ariz.

[*] Notice: The portion of the term of this patent subsequent to Dec. 22, 2004 has been disclaimed.

[21] Appl. No.: 89,865

[22] Filed: Aug. 27, 1987

Related U.S. Application Data

[63] Continuation of Ser. No. 759,453, Jul. 25, 1985, Pat. No. 4,714,473.

[51] Int. Cl.$^5$ .............................................. A61F 2/38
[52] U.S. Cl. ...................................................... 623/20
[58] Field of Search ...................... 623/20, 18, 21, 22, 623/23

[56] References Cited

U.S. PATENT DOCUMENTS

| | | |
|---|---|---|
| 3,715,763 | 2/1973 | Link . |
| 3,728,742 | 4/1973 | Averill . |
| 3,774,244 | 11/1973 | Walker . |
| 3,816,855 | 6/1974 | Saleh . |
| 3,837,009 | 9/1974 | Walker . |
| 3,840,904 | 10/1974 | Tronzo ................................. 623/22 |
| 3,849,805 | 11/1974 | Leake et al. . |
| 3,868,730 | 3/1975 | Kaufer et al. . |
| 3,869,731 | 3/1975 | Waugh et al. . |
| 3,879,767 | 4/1975 | Stubstad . |
| 3,896,502 | 7/1975 | Lennox . |
| 3,909,854 | 10/1975 | Martinez . |
| 3,916,451 | 11/1975 | Buechel et al. . |
| 3,919,723 | 11/1975 | Heimke et al. . |
| 3,945,053 | 3/1976 | Hillberry et al. . |
| 3,964,106 | 6/1976 | Hutter, Jr. et al. . |
| 3,975,778 | 8/1976 | St. Newton, III . |
| 3,977,026 | 8/1976 | Battault . |
| 3,986,212 | 10/1976 | Sauer . |
| 4,000,525 | 1/1977 | Klawitter et al. . |
| 4,011,602 | 3/1977 | Rybicki et al. . |
| 4,016,606 | 4/1977 | Murray et al. . |

(List continued on next page.)

FOREIGN PATENT DOCUMENTS

| 2122390 | 5/1971 | Fed. Rep. of Germany . |
| 2061730 | 5/1981 | United Kingdom ................. 623/20 |

OTHER PUBLICATIONS

Brochure from *Intermedics* on the "APR Universal Hip System", 1984.
"Key References in Biomaterials: Bone/Biomaterial Interface in Orthopedic Joint Implants" from Journal of Biomedical Materials Research, vol. 18, 577–599 (1984) John Wiley & Sons, Inc.
Intermedics Orthopedics Brochure 1984.
Technical Monograph, 1984, by Roy D. Bloebaum, Lawrence D. Dorr, and Diane Moynes.

*Primary Examiner*—Richard J. Apley
*Assistant Examiner*—James Prizant
*Attorney, Agent, or Firm*—Kelly, Bauersfeld & Lowry

[57] ABSTRACT

An improved prosthesis particularly for use as a knee joint is designed for secure ingrowth attachment to cancellous bone and adjacent tissue without use of bone cement. The prosthesis comprises a tibial component and a femoral component shaped to accommodate articulatory knee joint motion and each including a base surface adapted for enhanced bone ingrowth attachment to cancellous bone of a resected tibia and femur, respectively. The base surface of each component includes an extended surface area protruding into a region of cancellous bone and subdivided into a plurality of attachment zones coated with a selected porous bone ingrowth material, wherein these attachment zones are bounded by uncoated shallow channels for draining fluid from the attachment interface to the exterior of the prosthesis. In addition, each base surface includes one or more relatively thin anchoring fins extending in a medial-lateral direction for improved locking against component rotation while avoiding stress shielding of the ingrowth attachment interface, thereby achieving improved ingrowth fixation.

2 Claims, 3 Drawing Sheets

U.S. PATENT DOCUMENTS

| | | | |
|---|---|---|---|
| 4,017,911 | 4/1977 | Kafesjian et al. . | |
| 4,038,703 | 8/1977 | Bokros . | |
| 4,052,754 | 10/1977 | Homsy . | |
| 4,055,862 | 11/1977 | Farliag . | |
| 4,081,866 | 4/1978 | Upshaw et al. . | |
| 4,085,466 | 4/1978 | Goodfellow et al. . | |
| 4,127,902 | 12/1978 | Homsy . | |
| 4,136,405 | 1/1979 | Pastrick et al. . | |
| 4,164,794 | 8/1979 | Spector et al. . | |
| 4,166,292 | 9/1979 | Bokros . | |
| 4,168,326 | 9/1979 | Broemer et al. | 623/20 |
| 4,177,524 | 12/1979 | Grell et al. . | |
| 4,193,140 | 3/1980 | Treace . | |
| 4,205,400 | 6/1980 | Shen et al. . | |
| 4,206,516 | 6/1980 | Pilliar . | |
| 4,207,627 | 6/1980 | Cloutier . | |
| 4,209,861 | 7/1980 | Walker et al. . | |
| 4,213,209 | 7/1980 | Insall et al. . | |
| 4,215,439 | 8/1980 | Gold et al. . | |
| 4,217,666 | 8/1980 | Averill . | |
| 4,224,697 | 9/1980 | Murray et al. . | |
| 4,231,120 | 11/1980 | Day . | |
| 4,231,122 | 11/1980 | Koeneman . | |
| 4,234,972 | 11/1980 | Hench et al. . | |
| 4,249,270 | 2/1981 | Bahler et al. . | |
| 4,262,368 | 4/1981 | Lacey . | |
| 4,272,855 | 6/1981 | Frey . | |
| 4,301,553 | 11/1981 | Noiles . | |
| 4,307,472 | 12/1981 | Morris . | |
| 4,309,488 | 1/1982 | Heide et al. . | |
| 4,309,778 | 1/1982 | Buechel et al. . | |
| 4,328,593 | 5/1982 | Sutter et al. . | |
| 4,351,069 | 9/1982 | Ballintyn et al. . | |
| 4,355,428 | 10/1982 | Deloison et al. . | |
| 4,355,429 | 10/1982 | Mittelmeier et al. | 623/20 |
| 4,385,405 | 5/1983 | Teinturier | 623/20 |
| 4,430,760 | 2/1984 | Smestad . | |
| 4,430,761 | 2/1984 | Niederer et al. . | |
| 4,462,120 | 7/1984 | Rambert et al. . | |
| 4,470,158 | 9/1984 | Papas | 623/20 |
| 4,479,271 | 10/1984 | Bolesky et al. . | |
| 4,501,031 | 2/1985 | McDaniel et al. . | |
| 4,549,319 | 10/1985 | Meyer | 623/20 |
| 4,714,473 | 12/1987 | Bloebaum | 623/20 |

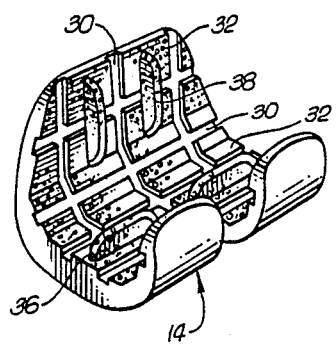
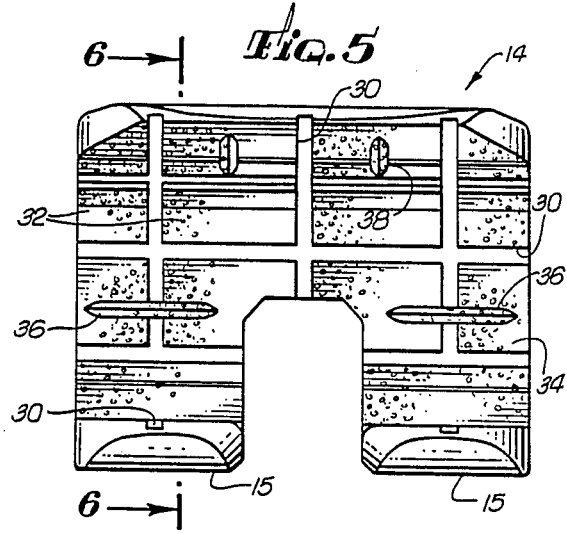
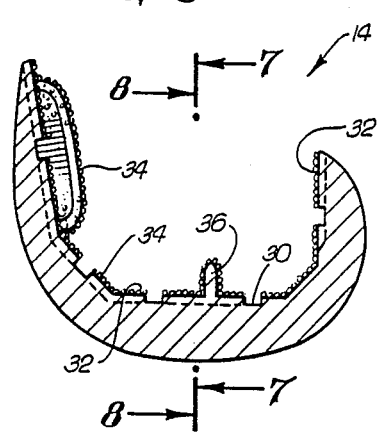
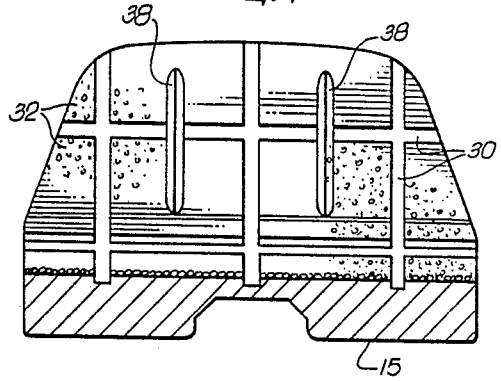
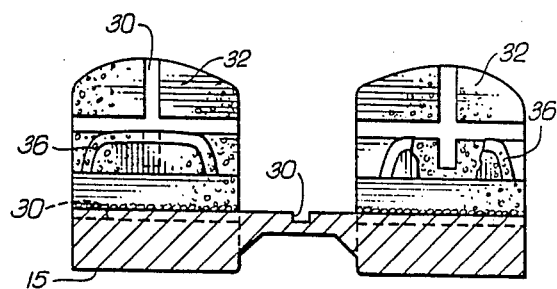

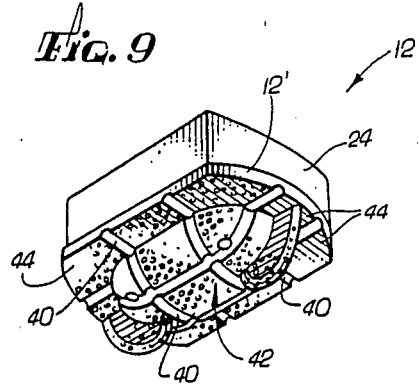
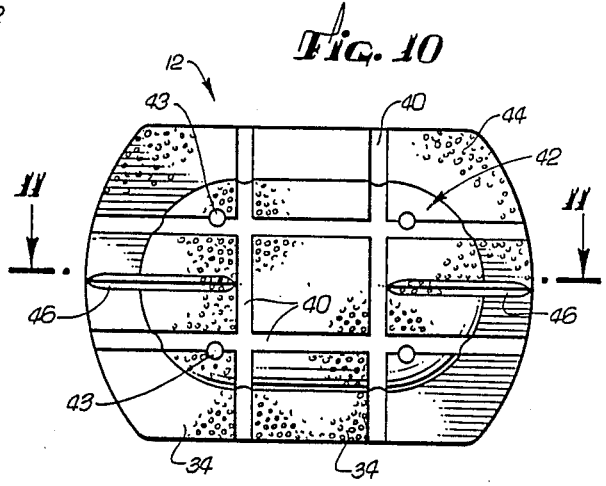
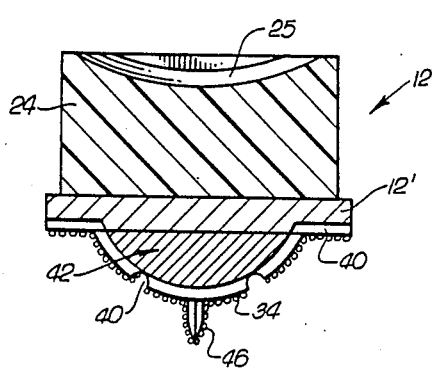
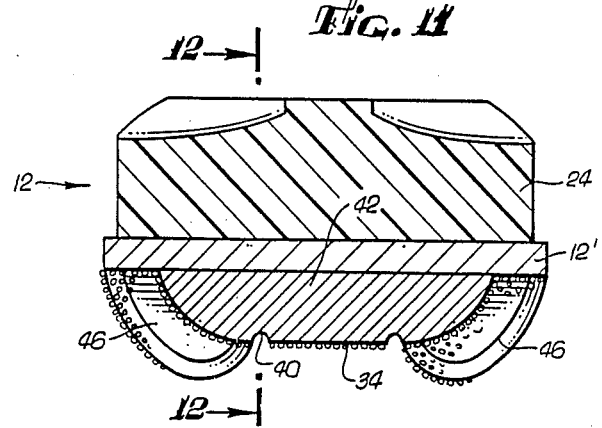

KNEE PROSTHESIS

This is a division of application Ser. No. 759,453 filed July 25, 1985 now U.S. Pat. No. 4,714,473, issued Dec. 22, 1987.

BACKGROUND OF THE INVENTION

This invention relates generally to improvements in prosthetic joints, such as knee joints and the like. More particularly, this invention relates to an improved joint prosthesis designed for enhanced fixation by means of direct ingrowth of bone and other living tissue, thereby avoiding use of fixating bone cements and the like.

Artificial or prosthetic joint mechanisms for implantation into animals, particularly humans, have been the subject of intensive research and development efforts for many years. Such prosthetic joint mechanisms have typically comprised one or more implant components formed from a relatively biostable material of selected structural properties and uniquely shaped to replace all or part of a selected anatomical joint, for example, a hip or knee joint. The implant components are installed by surgically accessing the joint and by resection of one or more bone surfaces to accommodate direct attachment thereto of the implant components. In the past, this bone attachment has been commonly achieved by use of bone cements, such as a methyl methacrylate-based cement or the like used as a grouting material to fill up the space between the receptive bone surface and the prosthetic component. In the process of its application, the cement interdigitates within the interstices of the bone surfaces to achieve mechanical fixation at the bone cement interface.

In recent years, a variety of potential disadvantages or limitations have been recognized with respect to cemented fixation of prosthetic joint mechanisms. More particularly, it is generally recognized that the use of bone cement to fixate prosthetic joint implant components provides a temporary securement which normally requires significant restrictions upon later patient activity to avoid failure of the cemented interface during the patient's lifetime. Failure of the cemented interface is especially undesirable, since the bone cement contributes to a significant degree of localized loss of bone structure which makes implantation of a secondary prosthesis extremely difficult and frequently impossible. These problems encountered by use of cemented prosthetic mechanisms are particularly severe with high load bearing, highly stressed joints, such as the knee joint.

In an effort to avoid use of bone cements, a variety of improved prosthetic joint mechanisms have been proposed for noncemented attachment to resected bone surfaces. Some of these noncemented mechanisms have envisioned enhanced mechanical attachments to the bone by means of press-fitted anchoring pegs and the like. Alternatively, other proposed joint mechanisms have suggested the use of attachment surfaces having closely controlled porosity characteristics designed for accommodating direct bone attachment by ingrowth of living cancellous bone or tissue. However, while these bone ingrowth proposals appear to offer significant advantages over previous cement fixated designs, the load-bearing capacity of ingrowth fixated prostheses has been limited, thereby preventing their widespread use at highly loaded and stressed joints, such as the knee, without requiring significant restrictions on subsequent patient activity to minimize risk of failure of the bone ingrowth interface.

There exists, therefore, a significant need for an improved joint prosthesis particularly adapted for use as a knee joint, wherein the prosthesis is designed for enhanced noncemented attachment to patient bone tissue and further wherein the prosthesis is configured to withstand high loading and stress thereby providing a prolonged service life. The present invention fulfills these needs and provides further related advantages.

SUMMARY OF THE INVENTION

In accordance with the invention, an improved prosthetic joint is provided for secure and stable attachment to patient bone by direct ingrowth of living bone and tissue, and without the use of a bone cement. The prosthesis comprises at least one implant component having a base surface defining an extended surface area subdivided into a plurality of attachment zones separated by relatively shallow channels. The attachment zones are coated with a selected material of controlled porosity designed for direct ingrowth attachment with cancellous bone and/or localized tissue to achieve secure biological fixation, whereas the channels are uncoated for draining accumulated fluid away from the attachment interface during an initial period of ingrowth.

In a preferred form of the invention, the improved prosthesis comprises a knee prosthesis including a tibial component or platform for attachment to the upper end of a patient's tibia and a femoral component for attachment to the lower end of a patient's femur. The tibial and femoral components are formed from a high strength biocompatible material, such as cobalt chrome or titanium alloy, with the tibial component typically supporting a bearing member of high density plastic or the like for engaging the femoral component to accommodate natural or near-natural knee flexion.

The tibial and femoral components each include a base surface presented in a direction toward the associated tibia or femur for attachment thereto. More particularly, the tibia and femur are surgically resected to expose cancellous bone and to matingly receive the tibial and femoral prosthetic components, respectively. The base surface of each component is positioned to protrude with extended surface area into contact with the exposed cancellous bone with the plurality of attachment zones defining controlled porosity ingrowth surfaces, such as an array of titanium or cobalt chrome spherical beads or titanium mesh or other known porous surface substances designed for bone and/or tissue ingrowth. Discontinuities and/or bulged protrusions are desirably included in said base surface for enhanced surface area. The shallow uncoated drainage channels bounding the attachment zones provide open paths conducting accumulated fluid and/or fluid-borne particulate to the exterior of the prosthesis and thus away from potential interference with secure bone ingrowth.

In accordance with further aspects of the invention, the base surface of each prosthetic component further includes at least one and preferably multiple anchoring fins seated into the resected bone. These anchoring fins are relatively thin and are oriented to extend generally in a radial direction relative to a central axis of the joint, preferably the medial-lateral direction, to provide extensive surface area resistive to rotational stress. These fins thus prevent component rotational shifting but do so with broad surface areas to avoid localized stress concentration at the fins, thereby resulting in improved ingrowth fixation at the attachment zone interfaces. In one form of the invention, these fins advantageously are also coated with the porous ingrowth material and thereby define additional attachment zones. Additional anchoring fins oriented to extend in the anterior-posterior direction may be provided as desired.

In use when the prosthesis is mechanically loaded, for example, during normal walking motion or the like, any tendency of the tibial or femoral bone surfaces to subside is accompanied by a macrolock interdigitation of the localized bone and tissue into the uncoated channels of the component base surfaces. This subsidence thus effectively increases the mechanical interlock with the prosthetic components and further enhances bone and-/or tissue ingrowth advancement into the porous attachment zone surfaces.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 4 is a perspective view showing the upper base surface of a femoral component comprising a portion of the knee prosthesis;

FIG. 5 is a top plan view of the femoral component of FIG. 4;

FIG. 6 is an anterior-posterior vertical section taken generally on the line 6—6 of FIG. 5;

FIG. 7 is a medial-lateral vertical section taken generally on the line 7—7 of FIG. 6;

FIG. 8 is a medial-lateral vertical section taken generally on the line 8—8 of FIG. 6;

FIG. 9 is a perspective view showing the lower base surface of a tibial component comprising a portion of the knee prosthesis;

FIG. 10 is a bottom plan view of the tibial component of FIG. 9;

FIG. 11 is a medial-lateral vertical section taken generally on the line 11—11 of FIG. 10; and FIG. 12 is an anterior-posterior vertical section taken generally on the line 12—12 of FIG. 11.

DETAILED DESCRIPTION OF THE PREFERRED EMBODIMENT

Figure 1:
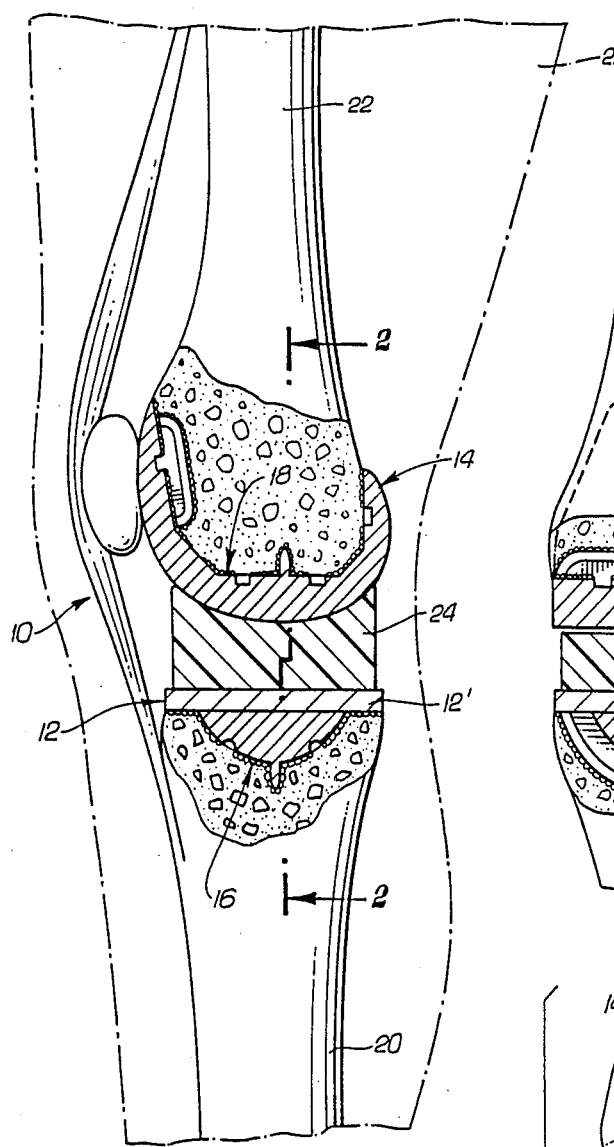
FIG. 1 is a side elevation view, partially in vertical section, illustrating a knee prosthesis embodying the novel features of the invention and implanted within the knee of a patient.

As shown in the exemplary drawings, an improved artificial joint is provided in the form of a knee prosthesis referred to generally by the reference numeral 10. The knee prosthesis 10 comprises a tibial component 12 interengageable with a femoral component 14 to accommodate natural or near-natural flexion of the knee joint. The tibial and femoral components 12 and 14 respectively include base surfaces 16 and 18 designed for enhanced fixation to the tibia 20 and to the femur 22 of a patient 23.

The improved prosthetic joint of the present invention advantageously provides highly stable fixation of prosthetic components directly to living bone tissue without requiring resort to bone cements or the like. Accordingly, the improved prosthetic joint may avoid the problems and/or limitations encountered with traditional cement fixated devices including, for example, the problems of temporary service life and localized losses of bone structure. Instead, the invention comprises a prosthesis of the type designed for noncemented biological fixation by bone and/or localized tissue ingrowth, wherein the invention provides an improved ingrowth configuration designed for highly secure and substantially permanent fixation, particularly when used in a severely loaded or stressed joint, such as the knee.

Figure 2:
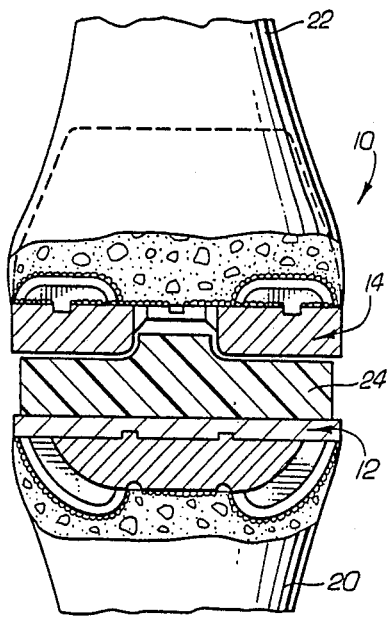
FIG. 2 is a medial-lateral vertical section taken generally on the line 2—2 of FIG. 1.
Figure 3:
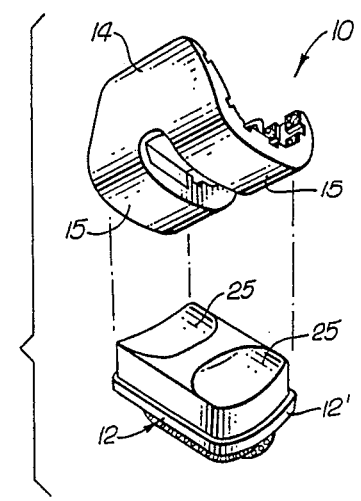
FIG. 3 is an exploded perspective view of the knee prosthesis.

As shown generally in FIGS. 1–3, the knee prosthesis 10 includes the tibial and femoral components 12 and 14 installed surgically at the upper and lower ends, respectively, of the patient's tibia 20 and femur 22. These components 12 and 14 are constructed generally from known biocompatible surgical implant materials, such as cobalt chrome or titanium alloys, stainless steel, composites, or other surgical implant materials known to those skilled in the art. The tibial component 12 traditionally provides an upper plateau or tray 12' defining a load-bearing structure which commonly supports a bearing member 24 of a high density plastic material, such as polyethylene or the like selected for relatively low friction engagement by the femoral component 14. The femoral component is commonly shaped to provide downwardly presented condylar surfaces 15 simulating the pre-surgical geometry of the femoral condyles and shaped for seated engagement within generally mating recesses 25 in the bearing member 24. The relative geometries of these condylar surfaces 15 and the bearing member recesses 25 are selected to accommodate natural or near-natural articulatory knee motion under natural muscle and ligament control. The specific geometries of these surfaces and the specific manner of supporting or fixating the bearing member on the tibial component 12 are generally known in the art and thus are not described in further detail herein.

The tibial and femoral components 12 and 14 of the improved knee prosthesis 10 are implanted generally in accordance with known surgical techniques. More particularly, the subject knee joint of the patient 23 is surgically accessed and the cortical bone defining the condylar surfaces of the tibia and femur at the knee joint are resected to expose underlying cancellous bone. Importantly, this surgical resection tailors the geometry of the tibia and femur to accommodate substantially mating and flush seated engagement with the base surfaces 16 and 18 of the tibial and femoral components 12 and 14, respectively, as viewed in FIGS. 1 and 2.

As shown in FIGS. 4–8, the base surface 18 of the femoral component 14 comprises an extended surface area for contacting the surgically exposed cancellous bone of the femur 22. This extended surface area is subdivided by a grid of relatively shallow and smooth channels 30 shown intersecting at right angles in a generally medial-lateral and anterior-posterior pattern with each channel 30 continuing uninterrupted to a side margin of the component. While the depths of these channels may vary, say within a range of from about 0.1 mm to about 3.0 mm, a channel depth of about 1.0 mm is contemplated for a knee prosthesis. The channels 30 thus bound a plurality of slightly raised attachment zones 32.

In the preferred form of the invention these attachment zones are each coated with a selected surface substance or ingrowth material 34 having a controlled porosity size and density for accommodating secure and stable post-surgical biological ingrowth of cancellous bone and/or localized tissue. The particular porous ingrowth material may vary, with examples of such materials comprising coatings of small spherical beads or fibers or other porous substances of a biologically compatible materials, such as titanium or cobalt chrome, thermoplastics, plasma sprays, and/or composite materials, such as blended hydroxy apatites and fibrous materials, and others. See, for example, U. S. Pat. Nos. 3,906,550; 4,000,525; 4,355,429; 4,479,271; 3,919,723; 4,038,703; 4,164,794; 4,168,326; 4,284,972; and 4,355,428, for disclosure of porous biological fixation materials, which are incorporated by reference herein.

The femoral component base surface 18 further includes a pair of upstanding anchoring fins 36 oriented to extend generally in a radial direction relative to a central axis of the femur and the joint. More particularly, the illustrative fins 36 extend in the medial-lateral direction to resist ingrowth fixated failure due to severe rotational stresses encountered at the knee joint. In the exemplary embodiment of the invention, these anchoring fins 36 are symmetrically disposed at centered anterior-posterior positions on opposite sides of a the central axis of the femur and may be coated on the anterior and posterior sides with the ingrowth material 34. These fins 36 advantageously provide an overall surface area presented anteriorly and posteriorly far exceeding the anterior/posterior area of conventional pegs. This configuration results in substantially wider distribution of rotational forces thereby achieving substantially enhanced resistance to rotational displacement. At the same time, the wide surface area of the fins avoids high localized stress concentration which can otherwise cause localized fixation limited predominantly to the region of the fins without adequate fixation at the interface with the attachment zones 32. Instead, the broad distribution of loading forces afforded by the fins 36 results in enhanced biological fixation at the attachment zones 32.

In addition, the femoral component 14 may include further anchoring fins 38 upstanding from the base surface 18 but oriented to extend, for example, generally in the vertical direction at an anterior segment of the femoral component. These additional fins 38 may also be coated with the porous ingrowth material and cooperate with the medial-lateral fins 36 to provide a high degree of resistance to rotational forces.

The base surface 16 of the tibial component 12 also includes a rectangular intersecting grid of relatively shallow channels 40, as viewed in FIGS. 9-12. These channels 40 extend over the underside of the tibial tray 12' and continue over a central downwardly bulged or bulbular protrusion 42 which can be attached to the tray 12' by pins 43 or integrally formed therewith and effectively increases the overall available surface area of the tibial component for contacting cancellous bone. The channels 40, which are similar in size to the channels 30 of the femoral component, thus subdivide the tibial component base surface 16 into a plurality of slightly raised attachment zones 44. Similar to the femoral component, the tibial attachment zones 44 are coated in the preferred form of the invention with the selected porous ingrowth material 34 to achieve biological fixation by bone and/or tissue ingrowth.

The base surface 16 of the tibial component also includes a pair of anchoring fins 46. As shown best in FIGS. 10 and 11, these fins 46 are oriented to extend in a radial direction relative to a central axis of the tibia, preferably in the medial-lateral direction from symmetric positions on opposite sides of the tibial central axis and at centered anterior-posterior positions. These tibial anchoring fins 46 thus provide extensive surface areas presented anteriorly and posteriorly to enhance resistance to rotation while widely distributing rotational forces in a manner avoiding stress concentrations potentially detrimental to ingrowth interdigitation at the attachment zones 44, as described previously with respect to the femoral component. If desired, these fins 46 are also coated with the ingrowth material 34.

When the tibial and femoral components 12 and 14 are surgically implanted, the joint is normally immobilized during a brief recovery period of perhaps 2-3 weeks during which the cancellous bone and/or localized tissue ingrows into and knits with the porous ingrowth material 34 to securely lock the components in place without requiring use of bone cement. Importantly, each component 12 and 14 has a substantial surface area located at a relatively shallow depth of a few millimeters within the resected bone whereat strong biological ingrowth is most likely to occur. The channels 30 and 40 comprise uncoated drainage channels bounding the attachment zones 32 and 44 and permit accumulated fluid and fluid-borne particulate or debris to flow away from the ingrowth interface thereby achieving a considerably stronger ingrowth attachment. Moreover, the anchoring fins provide broad surface areas presented in directions directly resisting rotational forces and stresses as encountered, for example, in a knee joint.

When the implanted prosthesis is subsequently loaded, for example, by normal patient walking motion, the prosthetic components 12 and 14 are compressively urged against the resected bone surfaces. Any tendency of these bone surfaces to subside over time in response to compressive loading is accompanied by reception of the bone and localized tissue into the drainage channels. This results in an increased mechanical macrolock between the prosthetic components and the bone, and further enhances increased microlock by advanced ingrowth penetration of bone and/or tissue into the porous ingrowth material.

The improved prosthetic joint of the invention thus provides enhanced prosthesis-bone interconnection without requiring use of bone cement. The prosthetic joint is particularly adapted for use as a knee joint to withstand the severe loading and twisting forces encountered during normal use.

A variety of modifications and improvements to the prosthetic joint of the invention are believed to be apparent to those skilled in the art. Accordingly, no limitation on the invention is intended by way of the description herein, except as set forth in the appended claims.

What is claimed is:

1. A prosthetic joint, comprising:
    a femoral component having a base surface for biological ingrowth attachment to the femur of a patient;
    a tibial component having a base surface for biological attachment to the tibia of a patient;
    said base surfaces of said femoral and tibial components each being defined by a plurality of relatively shallow and relatively smooth channels subdividing said base surfaces into a plurality of attachment zones, said attachment zones including a selected porous biological ingrowth material;

said base surface of said tibial component being further defined by a relatively flat tibial tray cooperating with and substantially surrounding a central outwardly bulged and smoothly contoured protrusion of a generally bulbular shape, said tray and protrusion together providing an extended surface area for contacting and biological ingrowth attachment to the tibia of a patient; and at least one anchoring fin member projecting downwardly from said base surface of said tibial component.

2. The prosthetic joint of claim 1 wherein said at least one anchoring fin member comprises a pair of anchoring fins oriented to extend generally in the medial-lateral direction and generally symmetric with respect to a central axis of the joint.

* * * * *